(12) United States Patent
Johnson et al.

(10) Patent No.: US 9,814,571 B2
(45) Date of Patent: Nov. 14, 2017

(54) ECM STRIP TO PLUG PERCUTANEOUS HEART VALVE LEAKS

(71) Applicants: Cook Medical Technologies LLC, Bloomington, IN (US); Cook Biotech Incorporated, West Lafayette, IN (US)

(72) Inventors: Chad E Johnson, West Lafayette, IN (US); Charles L. McIntosh, Silver Spring, MD (US)

(73) Assignees: Cook Medical Technologies LLC, Bloomington, IN (US); Cook Biotech Incorporated, West Lafayette, IN (US)

( * ) Notice: Subject to any disclaimer, the term of this patent is extended or adjusted under 35 U.S.C. 154(b) by 0 days.

(21) Appl. No.: 14/591,253

(22) Filed: Jan. 7, 2015

(65) Prior Publication Data

US 2015/0190226 A1    Jul. 9, 2015

Related U.S. Application Data

(60) Provisional application No. 61/924,813, filed on Jan. 8, 2014.

(51) Int. Cl.
*A61F 2/24* (2006.01)
*A61B 17/00* (2006.01)

(52) U.S. Cl.
CPC ............ *A61F 2/24* (2013.01); *A61B 17/0057* (2013.01); *A61B 2017/00004* (2013.01); *A61B 2017/00579* (2013.01); *A61B 2017/00592* (2013.01); *A61B 2017/00601* (2013.01); *A61B 2017/00619* (2013.01); *A61F 2/2409* (2013.01); *A61F 2210/0004* (2013.01); *A61F 2220/0008* (2013.01); *A61F 2250/0069* (2013.01)

(58) Field of Classification Search
CPC .... A61F 2/2418; A61F 2/2409; A61F 2/2412; A61F 2230/0054
See application file for complete search history.

(56) References Cited

U.S. PATENT DOCUMENTS

| 7,731,732 | B2 * | 6/2010 | Ken ................... A61B 17/0057 606/213 |
| 7,897,167 | B2 | 3/2011 | Armstrong et al. |
| 2006/1004442 | | 1/2006 | Spenser |
| 2008/0215087 | A1 | 9/2008 | Pavcnik et al. |
| 2009/0076547 | A1 * | 3/2009 | Sugimoto ........ A61B 17/00234 606/232 |
| 2010/0106178 | A1 | 4/2010 | Obermiller et al. |

FOREIGN PATENT DOCUMENTS

| WO | WO2007/005394 | 1/2007 |
| WO | WO 2009/029914 | 3/2009 |

* cited by examiner

*Primary Examiner* — Thomas J Sweet
*Assistant Examiner* — Tiffany Shipmon
(74) *Attorney, Agent, or Firm* — Woodard, Emhardt, Moriarty, McNett & Henry LLP (57) ABSTRACT

Described are devices and methods for medically sealing a perivalvular leak associated with implanted valves. For example, a bioresorbable tissue infiltratable sheet is provided for insertion through a perivalvular leak. A filament extending through the sheet is also provided which when pulled causes the sheet to gather around the filament on either side of the perivalvular leak. The gathered position of the sheet may be secured by a series of stops and/or use of a capping member.

16 Claims, 11 Drawing Sheets

ECM STRIP TO PLUG PERCUTANEOUS HEART VALVE LEAKS

CROSS-REFERENCE TO RELATED APPLICATION

This application claims the benefit of U.S. Provisional Application No. 61/924,813 filed Jan. 8, 2014, which is hereby incorporated by reference.

BACKGROUND

This disclosure concerns apparatuses and methods useful for sealing a perivalvular leak associated with an implanted heart valve. In particular, apparatus and methods are disclosed for percutaneously closing, and to promote healing of, an opening between the natural valve annulus and the wall of the implanted valve.

The human heart is a section of highly muscularized vasculature defining four chambers: the right atrium, the right ventricle, the left atrium, and the left ventricle. Each chamber is associated with a one-way valve for controlling the direction of blood flow. Blood flow is driven by pressure created by regular contraction (systole) and relaxation (diastole) of cardiac muscle. Contraction of the muscles surrounding the ventricles increases the pressure within the ventricular chamber driving blood through the one-way exit valve. When the chamber relaxes negative pressure is created which causes blood to flow in from the associated atria through the one-way entrance valve.

Deoxygenated blood is pulled into the heart via the right atrium, through the tricuspid valve, and into the right ventricle. During systole, ventricular pressure increases pushing deoxygenated blood out of the right atrium through the pulmonary valve. Blood is oxygenated in the pulmonary system and collects in the left ventricle. During diastole, oxygenated blood is pulled from the left atrium, through the mitral (or bicuspid) valve, and into the left ventricle. During systole, ventricular pressure increases pushing oxygenated blood out of the left ventricle through the aortic valve.

Each of the valves resist retrograde flow, for example, from the ventricles back to their corresponding atria or from the arteries back to their corresponding ventricles. Each valve is surrounded by an annulus comprising a dense fibrous ring which supports the valve. The collagenous ring of the annulus provides an anchor for the valve leaflets which must resist backflow pressure.

About 5 million Americans are diagnosed with heart valve disease every year. There are several types of heart valve disease, for example, valvular stenosis, and valvular insufficiency. Valvular stenosis occurs when the valve leaflets become stiff narrowing the valve opening and thus reducing the volume of blood that can pass through it. Valvular insufficiency occurs when the valve leaflets do not properly close allowing blood to flow retrograde across the valve.

It is well known to treat heart valve disease by replacing a diseased or damaged valve. The procedure, whether surgical or percutaneous, involves reshaping the annulus to receive a prosthetic heart valve (either bioprosthetic or mechanical). After implantation, perivalvular leaks can develop which allow backflow around the implanted valve between patient tissue and the implanted valve. These leaks can occur, for example, because the reshaped annulus does not conform to the shape of the implanted valve. Another cause may be an accumulation of calcium plaques on natural valve surfaces. When the annulus is expanded, in preparation for implantation, calcium deposits can fracture creating irregularities in the implantation site. Perivalvular leaks can result in diminished valve function, loss of blood pressure, increased stress on the heart, and hemolytic anemia. A need therefore exist for improved and/or alternate devices and systems for closure of perivalvular leaks.

SUMMARY

In certain aspects, the present disclosure provides unique medical devices and techniques which can effectively treat perivalvular leaks. In accordance with some forms of the disclosure, such medical devices are configured to utilize extracellular matrix material to occlude and promote healing of perivalvular leaks. Accordingly, in one embodiment, the present disclosure provides a device for obstructing a perivalvular leak associated with an implanted valve. The device includes a closure element comprising a bioresorbable tissue infiltratable sheet sized and configured for percutaneous delivery through a perivalvular leak. The device further includes a series of apertures spaced between a first and second end, and one or more filaments slidably extending through the apertures. The device is configured to be gatherable over the filaments from a first longer condition to a second condition defined by a first gathered region on a first side of the leak, an intermediate region extending through the leak, and a second gathered region on a second side of the leak. In accordance with certain forms of practicing the disclosure, the closure element is comprised of extracellular matrix material. In one embodiment the filament(s) is attached to the closure element. Certain inventive variants include one or more attachment elements configured to secure the closure element to the vessel wall.

In one form, the disclosed device contains one or more caps having a filament channel configured to receive one or more filaments. In one embodiment the cap is composed of a bioresorbable material. In certain modes of practicing the disclosure, the filament(s) further comprise one or more stops configured to frictionally engage the capping element. In one aspect, the channel and/or filament are configured such that the filament passes through the channel in a first direction but resists passage back through the channel in a second direction. In one aspect, the filament is composed of bioresorbable material.

In another embodiment the disclosure provides a method for closing a perivalvular leak. Such method comprises delivering a closure device to a perivalvular leak. The closure device comprising, an elongate strip of bioresorbable tissue infiltratable material sized and configured to transverse a perivalvular leak and containing one or more filaments slidably associated with the material. The method also includes inserting the closure device through the perivalvular leak so that a portion extends from either side of the leak with a portion transversing the leak. The method further includes deforming the strip of extracellular matrix material on each side of the leak. In some forms the bioresorbable tissue infiltratable material comprises extracellular matrix material.

In some forms, the disclosed method further includes attaching the closure device to the vessel wall. In certain embodiments the disclosed method further includes securing the position of the closure device on the filament. In certain embodiments a capping element containing a filament channel may be advanced over the filament.

In yet another embodiment the disclosure provides a method for closing a perivalvular leak comprising inserting a cannulated device through the perivalvular leak. The method further includes deploying a closure device on the far side of the leak, the device comprising a strip of bioresorbable tissue infiltratable material sized and configured to pass through a perivalvular leak and containing one or more filaments slidably extending through a series of openings. The method further includes deforming the material on the far side of the leak, expanding its cross-sectional profile. The method further includes retracting the cannulated device through the perivalvular leak and deploying a second portion of the closure device on the near side of the leak, with a portion of the device extending through the leak. The method further includes deforming the material on the near side of the leak, expanding the cross-sectional profile of the second portion. In some forms, the bioresorbable tissue infiltratable material comprises extracellular matrix material.

In some forms, the disclosed method further includes attaching the closure device to the vessel wall on the far and/or near side of the leak. In certain embodiments the disclosed method further includes securing the position of the closure device on the filament such that the closure device maintains an expanded cross-sectional profile. Certain inventive variants further include the step of introducing a cap over the filament, the cap containing a filament channel to receive the filament.

Additional embodiments, as well as features and advantages of the disclosed embodiments, will be apparent from the description herein.

DESCRIPTION OF THE SELECTED EMBODIMENTS

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

Figure 1:
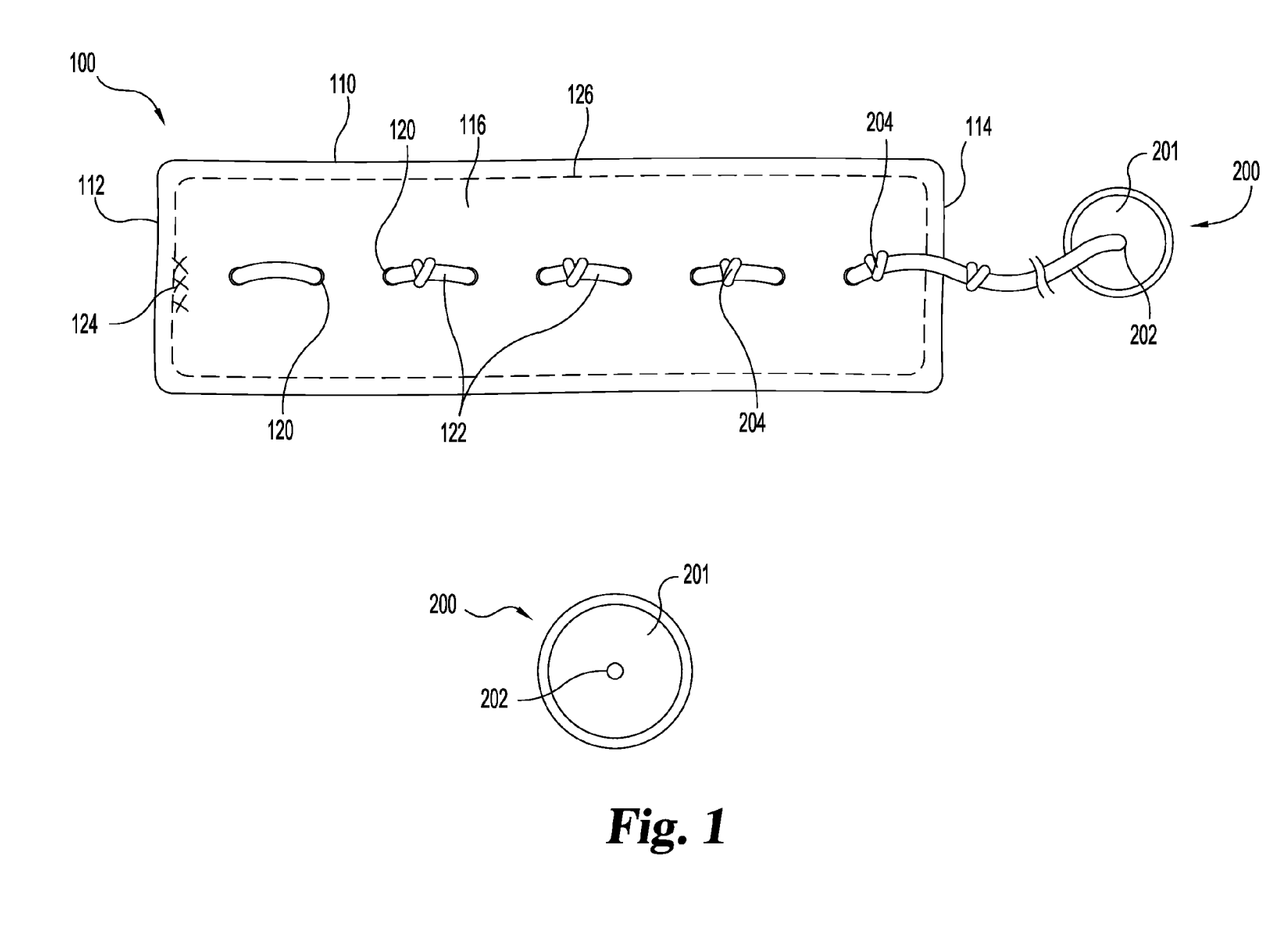
FIG. 1 provides a top view of one embodiment of the disclosed device along with a side view of an embodiment of the disclosed capping element.
Figure 2:
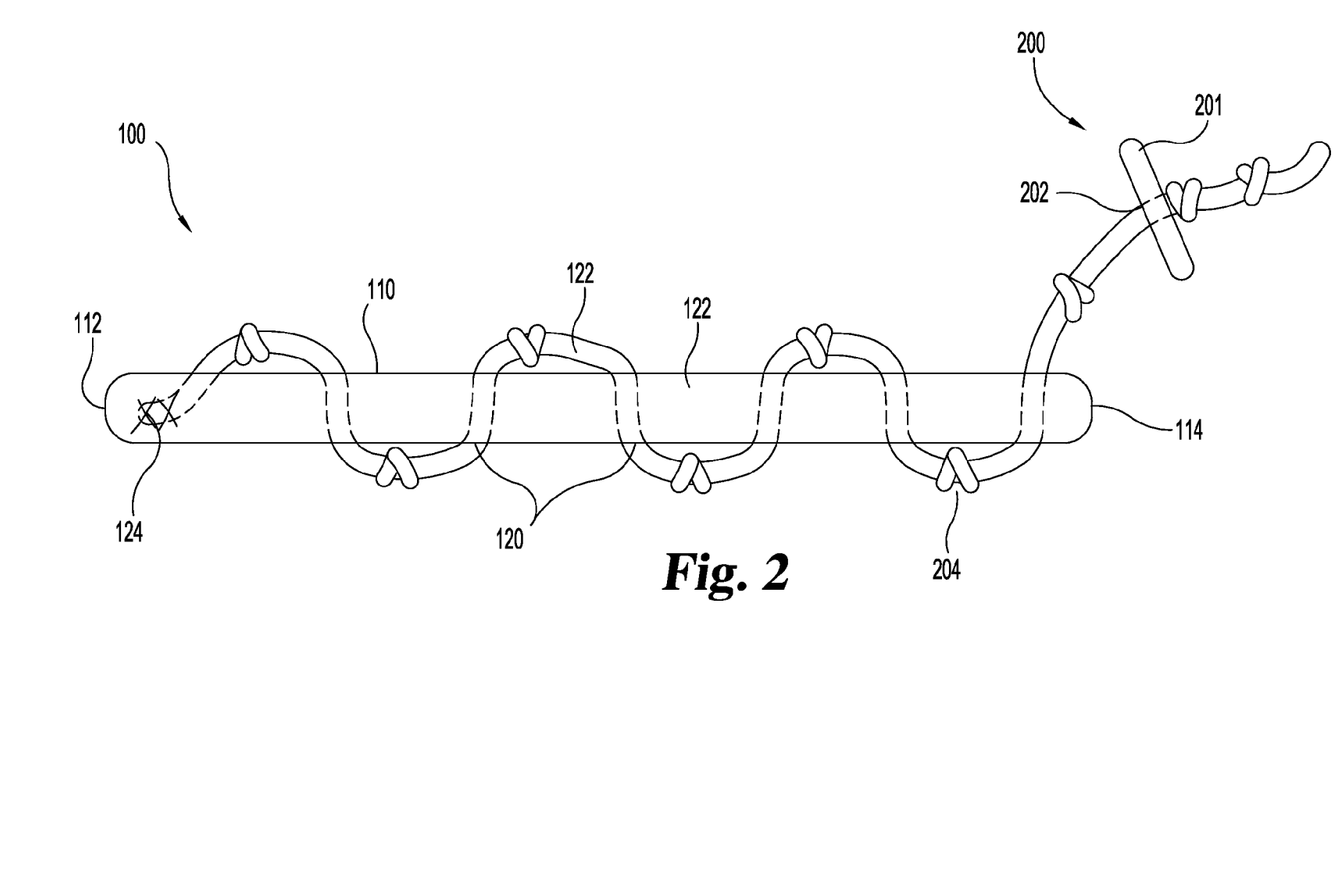
FIG. 2 provides a side view of one embodiment of the disclosed device.

With reference now to FIGS. 1 and 2, a device 100 for obstructing perivalvular leak includes closure element 110, capping element 200 and filament 122. Closure element 110 comprises bioresorbable tissue infiltratable sheet material 116 having a first end 112 and a second end 114. In some forms, apertures 120 extend between first end 112 and second end 114. In certain embodiments, perimeter stitching 126 is provided to reinforce bioresorbable tissue infiltratable sheet material 116. In some forms, filament 122 is slidable through apertures 120. In certain embodiments filament 122 is attached to closure element 110 at a filament attachment site 124. In some forms, filament 122 may also comprise stops 204. Capping element 200 comprises a body 201 and filament channel 202. In some forms filament 122 passes through filament channel 202.

Figure 3:
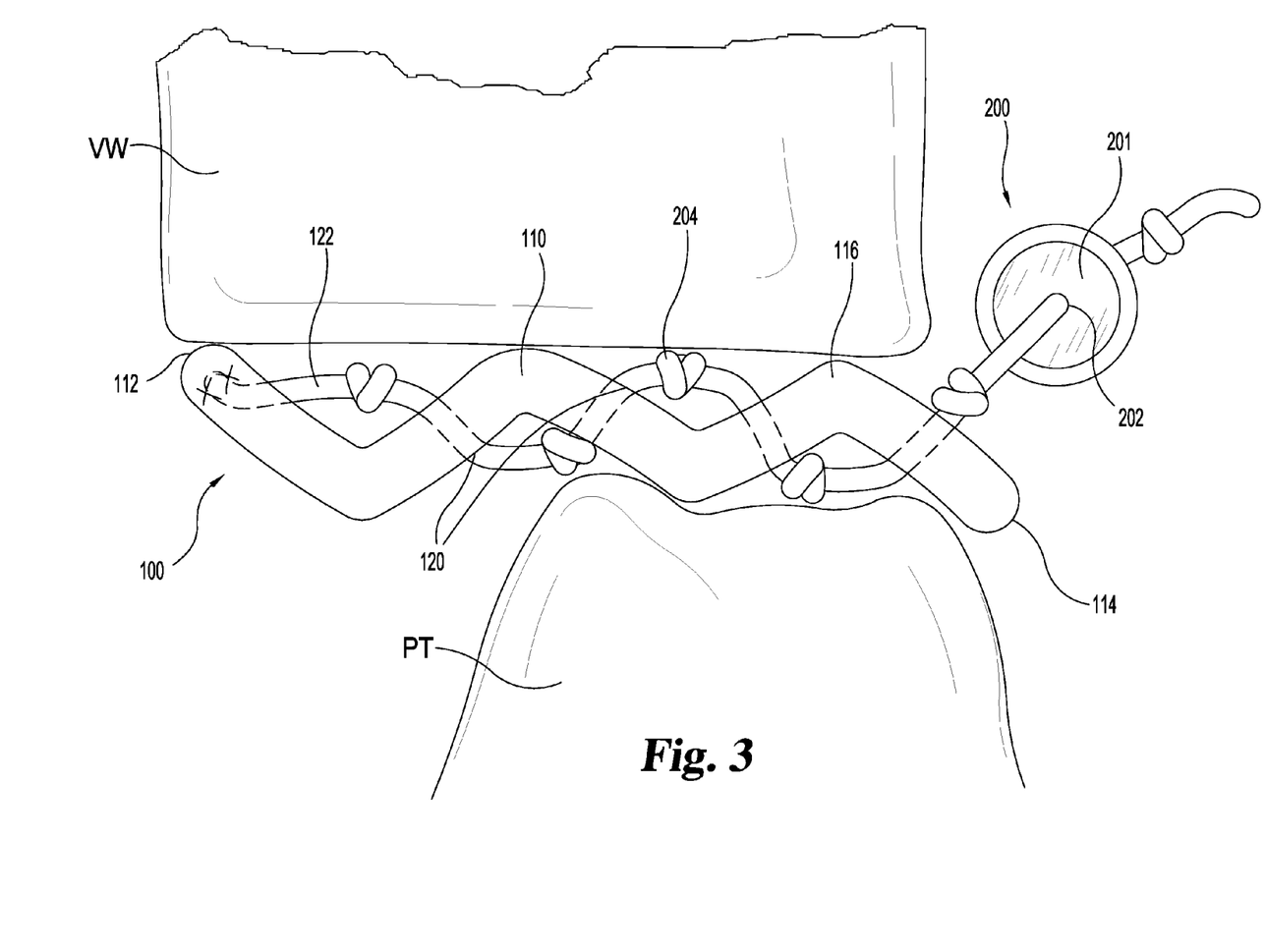
FIG. 3 provides a view of one embodiment of the disclosed device inserted within a perivalvular leak.

With reference now to FIG. 3, there is depicted a device 100 for obstructing a perivalvular leak partially deployed within a perivalvular leak. A perivalvular leak spans between the valve wall VW of an implanted valve and patient tissue PT. Closure element 110 has a first end 112 and a second end 114. In certain embodiments, first end 112 is inserted from the proximal to the distal side of the perivalvular leak while second end 114 remains on the proximal side of the perivalvular leak. Closure element 110 further comprises bioresorbable tissue infiltratable sheet material 116. In some forms, bioresorbable tissue infiltratable sheet material 116 comprises extracellular matrix material. In some forms, the disclosed device 100 further comprises filament 122, and/or apertures 120. In some forms, stops 204 are located within or upon filament 122. In some forms, filament 122 passes through filament channel 202 of capping element 200. In some forms, capping element 200 further comprises body 201.

Figure 4:
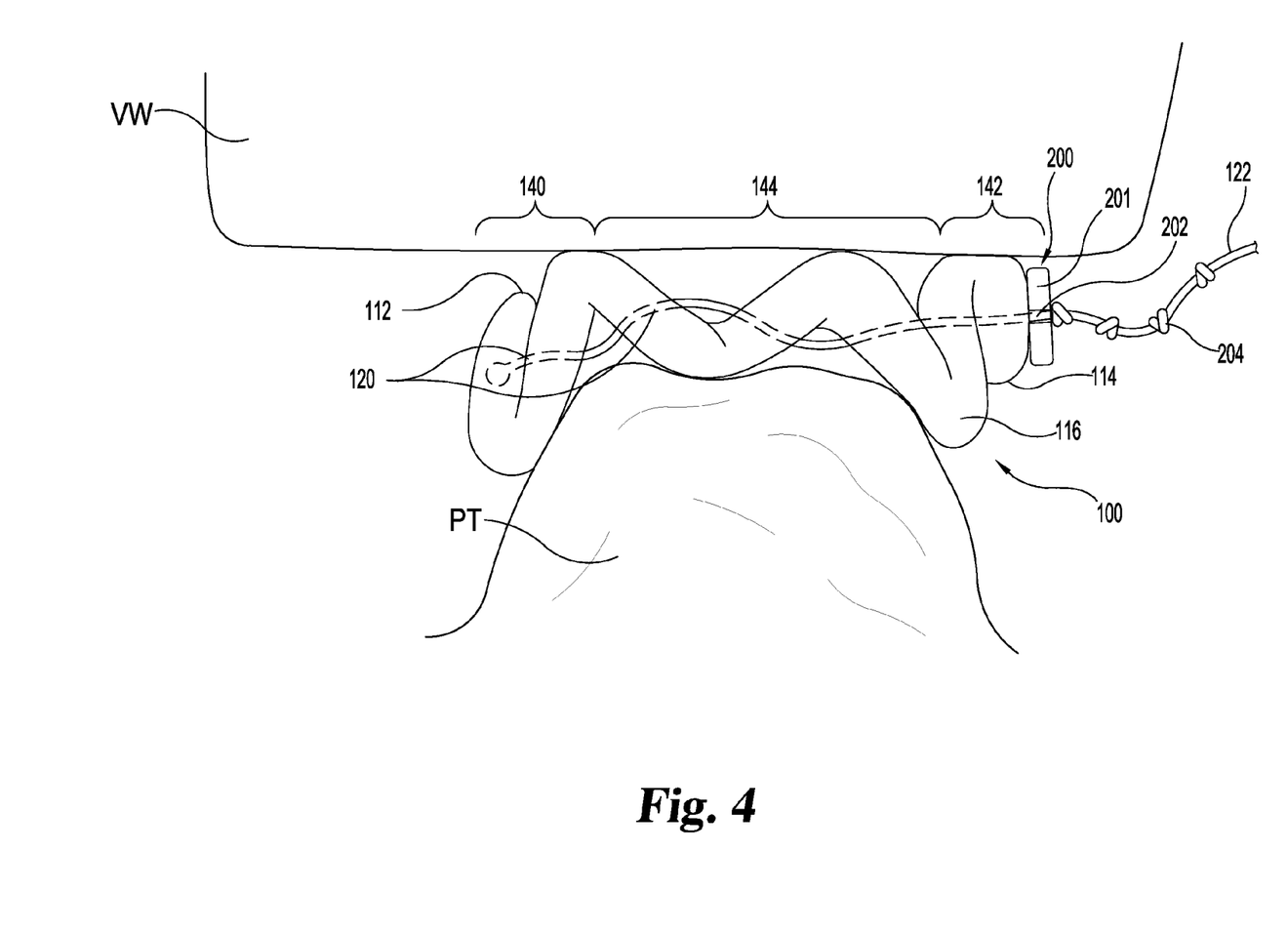
FIG. 4 provides a view of one embodiment of the disclosed device secured within a perivalvular leak.

With reference now to FIG. 4 which illustrates the device 100 for obstructing a perivalvular leak deployed within a perivalvular leak between valve wall VW and patient tissue PT. The deployed valve has a first gathered portion 140 which includes first end 112, an intermediate region 144, and a second gathered portion 142 which includes second end 114. In some forms, filament 122 spans from said first gathered portion 140 through intermediate region 144 to second gathered portion 142. In some forms, capping element 200 retains closure element 110 in this gathered state by securing filament 122 in filament channel 202.

In certain embodiments apertures 120 comprise holes through said bioresorbable tissue infiltratable sheet material 116. Other configurations suitable for gathering or bunching the material are envisioned. Certain non-limiting examples include attaching rings or loops to material 116, and attaching a tunnel-like sheet to material 116.

Figure 5:
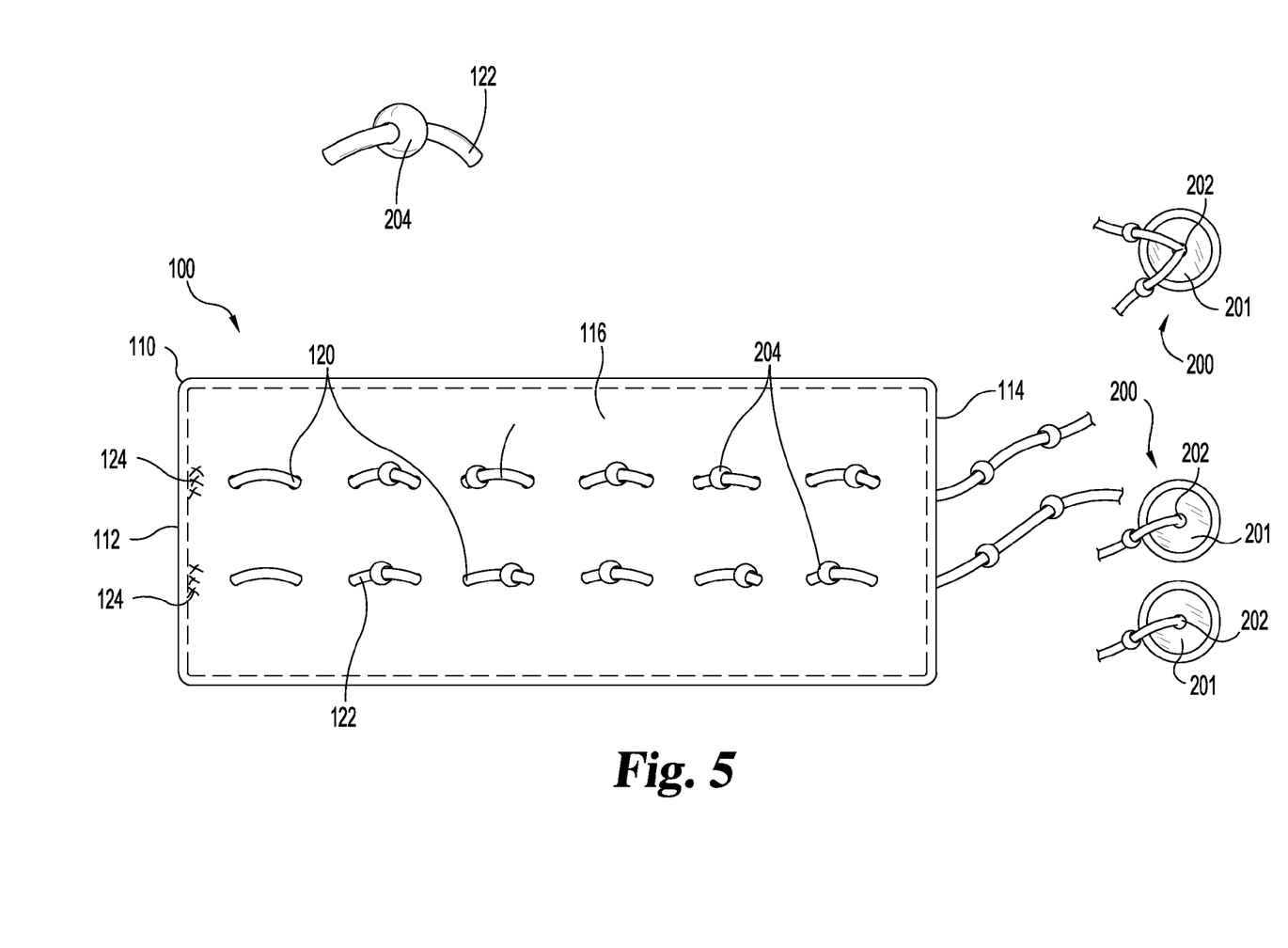
FIG. 5 provides a top view of one embodiment of the disclosed device with alternative capping element embodiments.

As shown in FIG. 5, device 100 may include two or more filaments 122. In certain embodiments, filaments 122 are composed of a bioresorbable synthetic material such as, for example, polylactic-co-glycolytic acid. In some forms, filaments 122 are comprised of non-resorbable biocompatible material such as nitinol or non-resorbable synthetic polymers. In some forms, filaments 122 may be composed of a naturally occurring material such as, for example, extracellular matrix material. In some forms, filaments 122 may be attached to device 100 proximate to first end 112 of device 100. Exemplary methods of attachment include, for example, stitching or use of a biologically compatible adhesive. Filaments 122 may be attached, for example, between laminates of bioresorbable tissue infiltratable sheet material 116 or may also be attached on an exterior surface of bioresorbable tissue infiltratable sheet material 116. In certain embodiments, for example when two or more filaments 122 are present, filaments 122 may be interconnected proximate the distal end of device 100 forming a continuous filament, such that device 100 gathers over filaments 122 when deployed. In yet another form, filaments 122 may extend beyond the distal end of device 100 such that filaments 122 may be secured to a vessel or valve wall to allow gathering of the device 100 over filaments 122. It is also envisioned that a retention element similar to capping element 200 may be included on the distal side of device 100. Such retention element may be configured to secure distal end of filaments 122 proximate the distal end of bioresorbable tissue infiltratable sheet material 116.

In some forms, filaments 122 contain stops 204 configured to pass through filament channel 202 of capping element 200 in a first direction, for example to allow capping element to move towards the first end 112 of closure element 110. In certain embodiments, stops 204 are configured to resist filament passage back through filament channel 202 of capping element 200 in a second direction, for example sliding capping element 200 away from the first end 112 of closure element 110. In some forms, stops are configured to be monolithic with filaments 122, for example, comprising knots or serrations of the filament. In other forms, stops are added to filaments 122, for example beads or buttons. In some forms stops 204 are composed of a bioresorbable synthetic material, for example, polylactic-co-glycolytic acid. In other embodiments, filaments 122 may be composed of a self-anchoring suture material which contains bi-directional barbs in a monofilament material. Such embodiments would allow passage of filament through apertures 120 and filament channel 202 in a first direction and resist passage of filament 122 through apertures 120 and filament channel 202 in a second direction. In another embodiment, filaments 122 may be composed of a shape memory material, such as nitinol.

As shown in FIG. 5 in embodiments utilizing two or more filaments 122, one or more capping elements 200 may be utilized. In some forms, capping element 200 is configured to receive one or more filaments through filament channel 202. In another illustrative embodiment, each filament 122 is associated with a separate capping element 200. It is also envisioned that a single capping element 200 may include one or more filament channels 202 for receiving multiple filaments.

In some forms, capping element 200 may be composed of a biological material such as a bioresorbable tissue infiltratable material, for example, extracellular matrix material. In other forms, capping element 200 may be composed of a synthetic material. In some forms, the synthetic material is bioresorbable, for example, polylactic-co-glycolytic acid. Capping element 200 may comprise a disc or any other shape suitable for securing position of closure element 110 on filament 122. For example, capping element 200 may be box-shaped, cylindrical, conical, or spherical. In other forms capping element 200 may comprise a clip-like structure which frictionally engages filament 122.

Figure 6A:
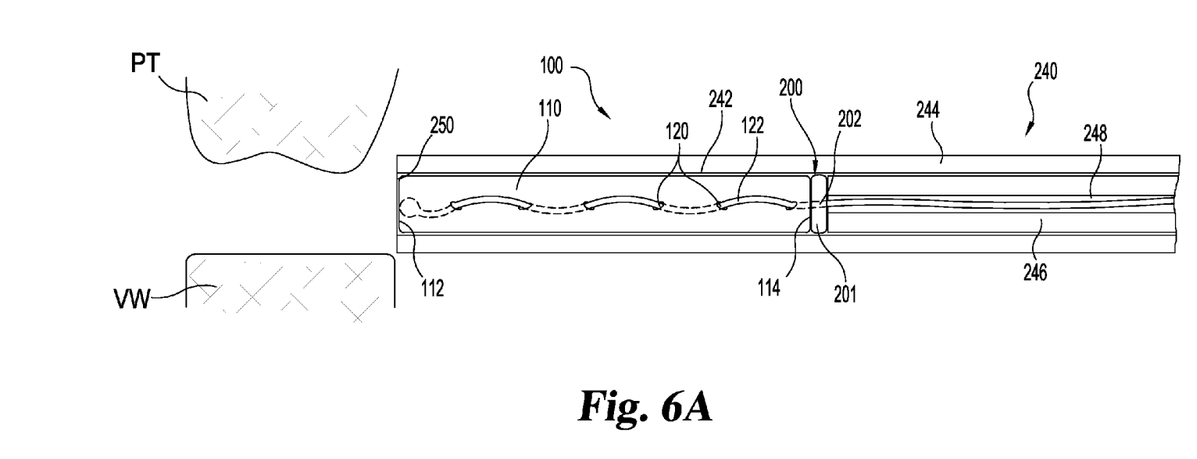
FIG. 6A provides a side view of one embodiment of the disclosed device loaded within a cannulated device and delivered to the site of a perivalvular leak.

Turning now to FIGS. 6A-6F there is depicted a method for obstructing a perivalvular leak. FIG. 6A depicts device 100 loaded within a cannulated device 240, the device having an inner lumen 242 surrounded by a wall 244, and distal opening 250. In some forms, wall 244 is cylindrical. In other forms, wall 244 is oblong in cross-section. Cannulated device 240 may also include pusher element 246. In some forms, pusher 246 includes pusher filament passage 248.

Figure 6B:
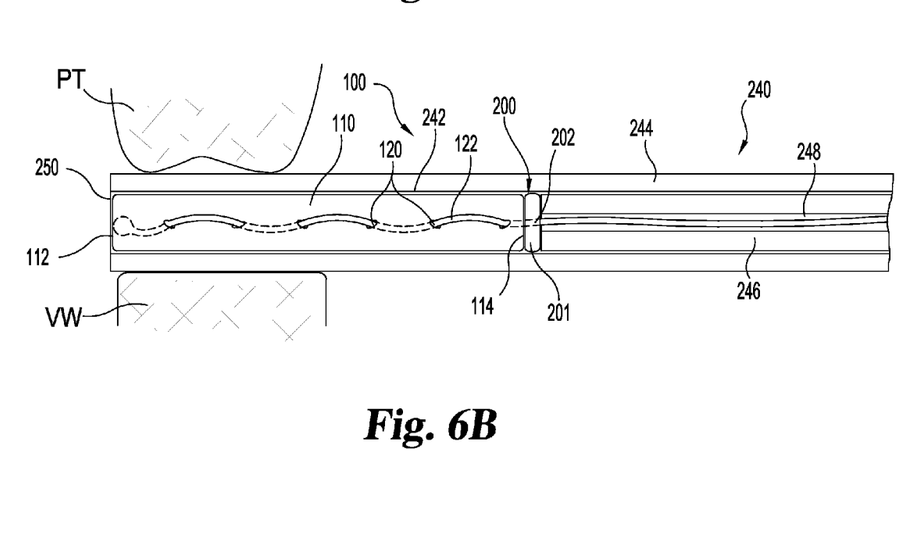
FIG. 6B provides a side view of one embodiment of the disclosed device loaded within a cannulated device pushed through a perivalvular leak.
Figure 6C:
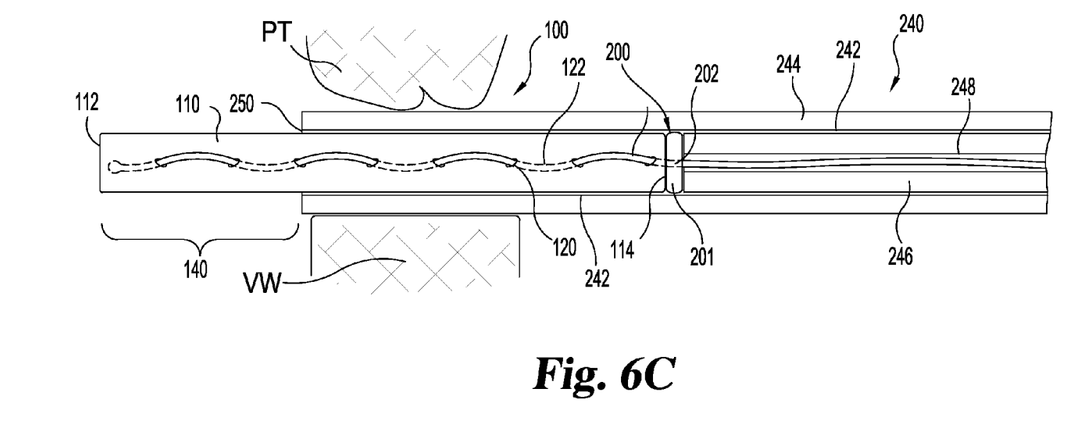
FIG. 6C provides a side view of one embodiment of the disclosed device in which a first portion is deployed from the cannulated device.
Figure 6D:
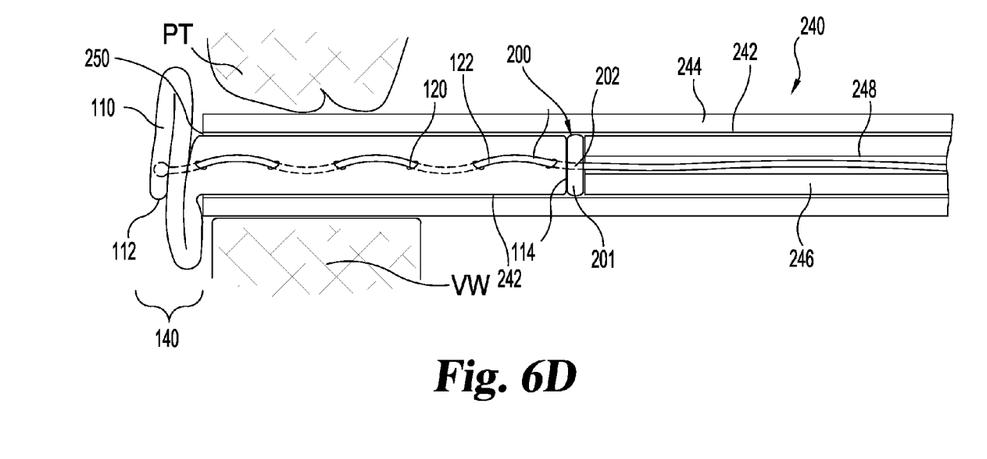
FIG. 6D provides a side view of one embodiment of the disclosed device in which the first portion has been expanded.
Figure 6E:
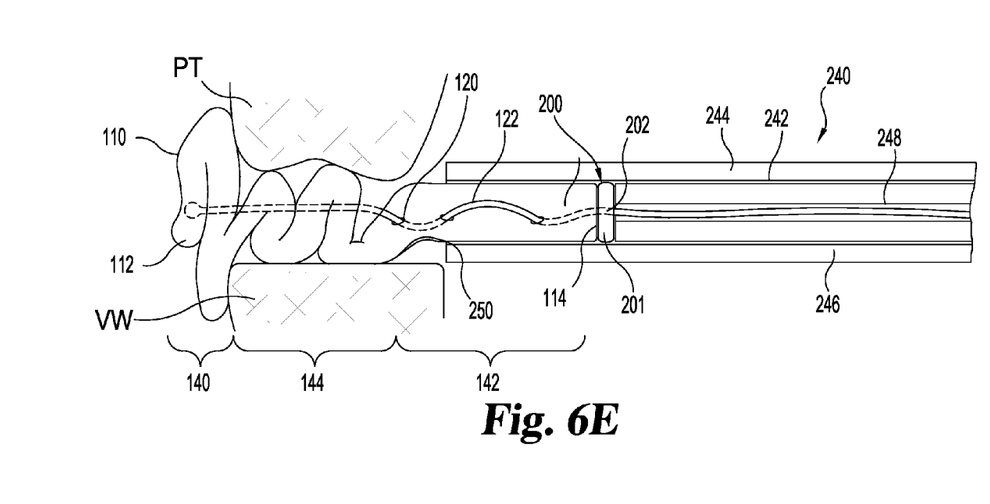
FIG. 6E provides a side view of one embodiment of the disclosed device in which the cannulated device has been further retracted and an additional portion of the disclosed device has been deployed through the perivalvular leak.
Figure 6F:
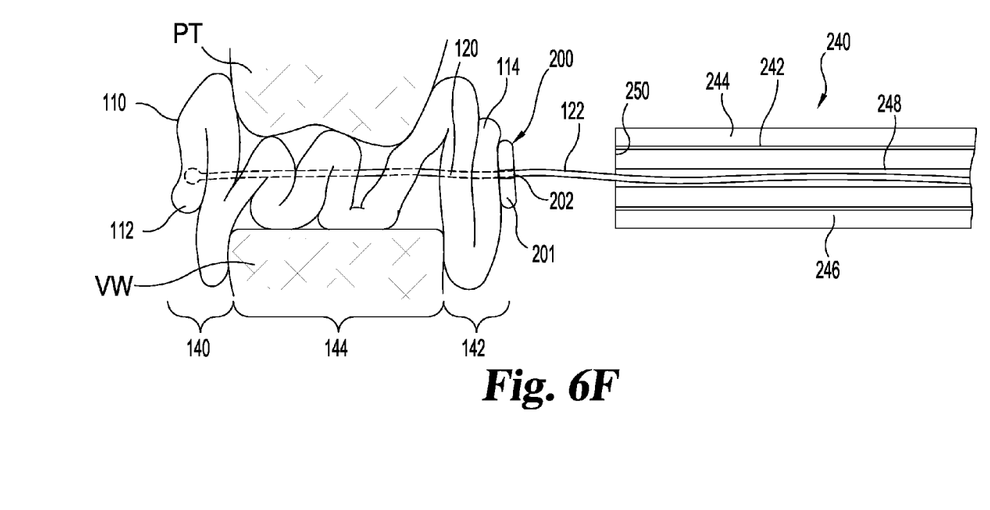
FIG. 6F provides a side view of one embodiment of the disclosed device in which the disclosed device has been secured within a perivalvular leak.

In use, cannulated device 240 is delivered through a perivalvular opening between patient tissue PT and valve wall VW as depicted in FIG. 6B. A first portion 140 of closure element 110 is advanced through distal opening 248 from cannulated device 240 on the distal side of the perivalvular leak. Filament 122 may then be pulled or retracted causing first portion 140 of device 100 to gather around filament 122 on the distal side of the perivalvular leak as depicted in FIG. 6D. In some forms gathering may be caused by advancing capping element 200 distally along filament 122. While maintaining tension on filament 122, cannulated device 240 may be further retracted while deploying a second portion 144 of device 100 through the perivalvular leak. The disclosed method further includes the step of deploying a third portion 142 of device 100, which contains second end 114 on the proximal side of the perivalvular leak. In accordance with some forms of the disclosure, pusher 246 may be utilized to push closure element 110 from the cannulated device 240. Pusher 246 may also push capping element 200 against device 100 while further tensioning filament 122 causing proximate side of device 100 to gather around filament 122 as depicted in FIG. 6F.

In accordance with some forms of practicing the disclosure, the distal side of device 100 may be attached to either the vessel wall or to the implanted valve wall prior to retracting cannulated device 240. In some forms, the proximal end of device 100 and/or filaments 122 may also be attached and secured to the vessel or implanted valve wall.

Figure 7:
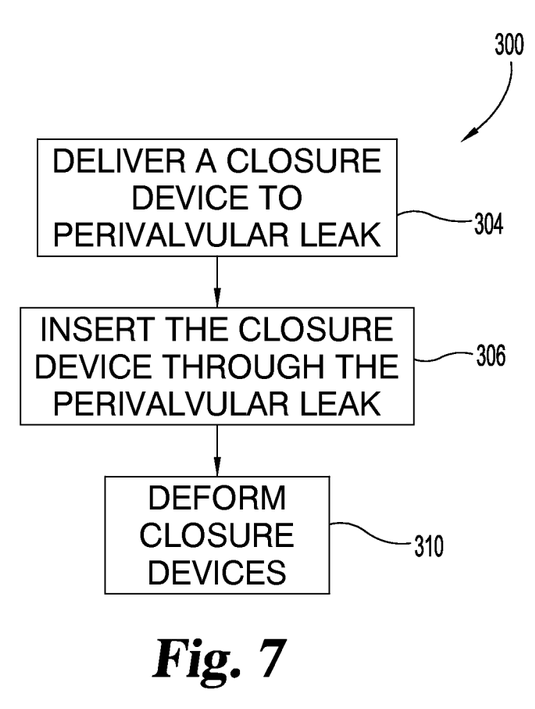
FIG. 7 provides a flow chart depicting one embodiment of the present disclosure for closing a perivalvular leak.

Turning now to FIG. 7 which illustrates a method 300 for obstructing a perivalvular leak, in a first step 304, a device 100 for obstructing a perivalvular leak is delivered to a perivalvular leak. In some forms of practicing the disclosure, step 304 may be accomplished, for example, by advancing a guide wire through a perivalvular leak. The method also includes a step 306 of inserting the closure device 100 through the perivalvular leak. In accordance with some forms of practicing the disclosure, device 100 may be attached to vessel and/or valve walls. Once inserted through the perivalvular leak, method 300 further includes step 310 deforming closure device 100 which increases the cross-sectional profile of the device 100 as the bioresorbable tissue infiltratable sheet material 116 gathers around filament 122 on the proximal and/or distal side of the perivalvular leak. In some forms, device 100 may also increase in cross-sectional profile within the perivalvular leak. Certain modes of practicing the disclosed method further include the step 308 of pulling the filament.

Figure 8:
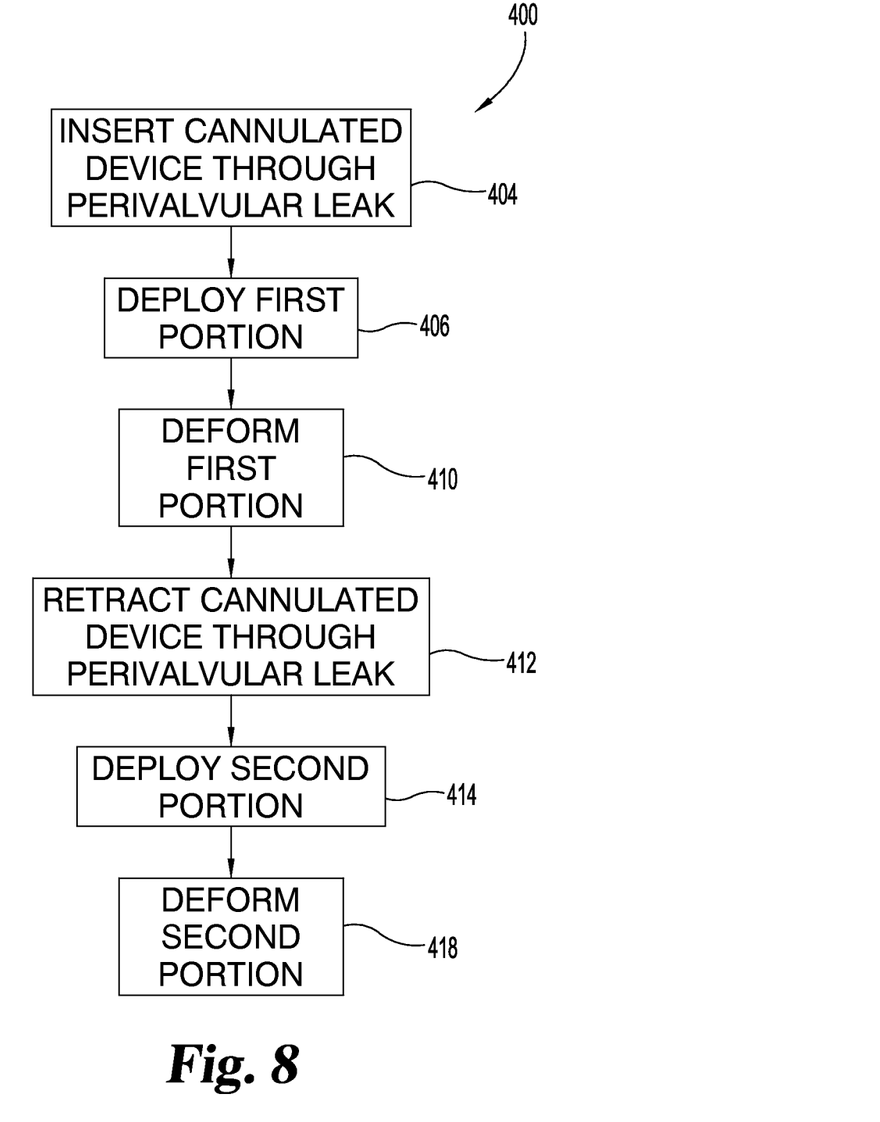
FIG. 8 provides a flow chart depicting one embodiment of the present disclosure for closing a perivalvular leak.

With reference now to FIG. 8 which illustrates a method 400 for obstructing a perivalvular leak, the disclosed method includes a first step 404 inserting a cannulated device through a perivalvular leak. In a subsequent step 406, a first portion of a closure element is deployed on the distal side of a perivalvular leak. The method further includes step 410 of deforming the first portion. Deformation can be accomplished by, for example, pulling filament 122, or advancing closure device 200 distally along filament 122. In certain modes of practicing the disclosure, such deformation comprises a gathering of closure element 110 over filaments 122 creating an increase in cross-sectional profile of device 100. The method further includes step 412 of retracting the cannulated device through the perivalvular leak. In accordance with some forms of the disclosure, as the cannulated device is retracted, tension is maintained on filament 122 so as to retain the first deployed portion in its deformed state. In accordance with certain forms of practicing the disclosure, an intermediate region of device 100 is deployed throughout the perivalvular leak. The method also includes step 414 of deploying a second portion of the closure element on a proximal side of the perivalvular leak. The method further includes step 418 deforming the second portion. Deformation can be accomplished by, for example, pulling filament 122, or advancing closure device 200 distally along filament 122. In certain modes of practicing the disclosure, such deformation comprises a gathering of closure element 110 over filaments 122 creating an increase in cross-sectional profile of device 100. Certain modes of practicing the disclosed method further include the step 408/416 of pulling the filament.

In some forms, deforming closure element 110 causes bioresorbable tissue infiltratable sheet material 116 to gather around filament 122, thus increasing cross-sectional profile of device 100 leading to obstruction of the perivalvular leak. In accordance with some forms of practicing the disclosure, a first portion of closure element 110 may be secured to the vessel or valve wall on the distal side of the perivalvular leak. In accordance with certain forms of practicing the disclosure, the proximal end of closure element 110 may be secured to the valve or vessel wall on the proximal side of the perivalvular leak. In one embodiment, the method further includes a step of advancing a capping element 200 over filament 122 so as to secure closure element 110 in its gathered state.

Figure 9:
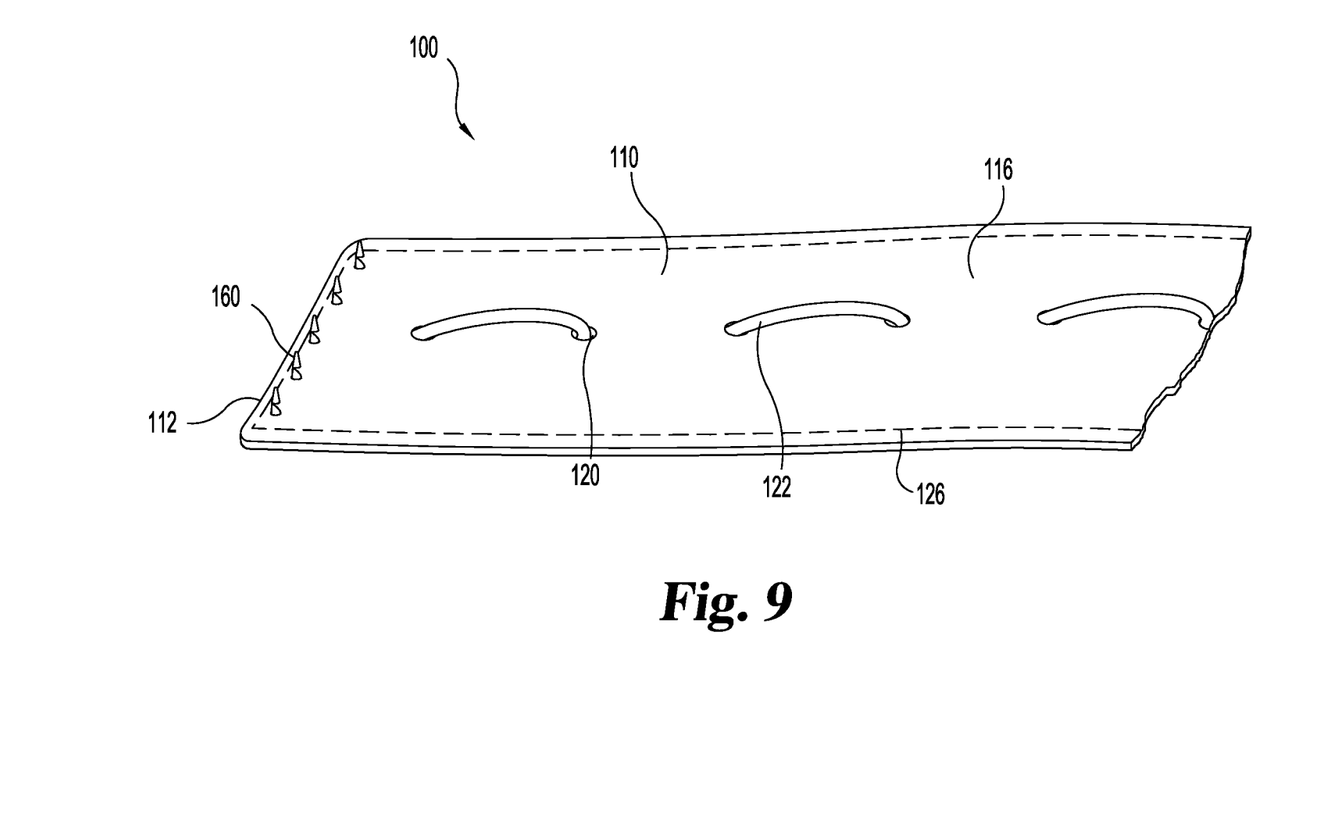
FIG. 9 provides a perspective view depicting one embodiment of the disclosed device.

Certain embodiments of the present disclosure include attachment elements 160 as illustrated in FIG. 9. Attachment elements 160 may be configured on or proximate to first end 112, second end 114, or throughout the length of closure element 110. Attachment element 160 may comprise barbs extending from the surface of closure element 110. Other forms for example, hooks, spikes, points, spears, spines, or adhesives are also envisioned. In some forms of the disclosed device, attachment elements 160 are deployed bilaterally on closure element 110. In some forms, attachment elements 160 are supported by, for example, a support member extanding between laminates of bioresorbable tissue infiltratable sheet material 116. Attachment elements 160 may be resorbable. In some forms of practicing the disclosure, attachment elements 160 are composed of a resorbable synthetic material such as polylactic-co-glycolytic acid. Attachment elements 160 may also comprise a biocompatible metal such as nitinol.

In certain embodiments, one or more device components will be comprised of a bioresorbable tissue infiltratable material. Particular advantage can be provided by devices that incorporate a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or in bodily regions in which inventive devices are implanted or engrafted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present disclosure can be obtained by harvesting such tissue sources and delaminating the submucosa-containing matrix from smooth muscle layers, mucosal layers, and/or other layers occurring in the tissue source. For additional information as to some of the materials useful in the present disclosure, and their isolation and treatment, reference can be made, for example, to U.S. Pat. Nos. 4,902,508, 5,554,389, 5,993,844, 6,206,931, and 6,099,567.

Submucosa-containing or other ECM tissue used in the disclosure is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 $\mu$g/mg, more preferably less than about 2 $\mu$g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present disclosure.

A typical layer thickness for an as-isolated submucosa or other ECM tissue layer used in the disclosure ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

The ECM tissue material may include one or more bioactive agents. Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the disclosure may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present disclosure can be derived from any suitable organ or other tissue source, usually sources containing connective tissues. The ECM materials processed for use in the disclosure will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the disclosure will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the disclosure.

The submucosa-containing or other ECM material used in the present disclosure may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature. Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufactured step, immediately prior to the procedure (e.g., by soaking the material in a solution containing a suitable antibiotic such as cefazolin), or during or after engraftment of the material in the patient.

Inventive devices can incorporate xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material(s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

In certain forms, inventive devices include a material receptive to tissue ingrowth. Upon deployment of such devices in accordance with the present disclosure, cells from the patient can infiltrate the material, leading to, for example, new tissue growth on, around, and/or within the device. In some embodiments, the device comprises a remodelable material. In these embodiments, the remodelable material promotes and/or facilitates the formation of new tissue, and is capable of being broken down and replaced by new tissue. Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any component of a medical graft product of the disclosure (including any ECM material) can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the disclosure, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

It is sometimes advantageous to perform drying operations under relatively mild temperature exposure conditions that minimize deleterious effects upon the ECM materials of the disclosure, for example native collagen structures and potentially bioactive substances present. Thus, drying operations conducted with no or substantially no duration of exposure to temperatures above human body temperature or slightly higher, say, no higher than about 38° C., will preferably be used in some forms of the present disclosure. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

In additional embodiments, graft elements useful in the disclosure can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a bodily segment within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typically such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of three-dimensionally stable shapes for use in the preparation of medical materials and devices. It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression similar to a non-expanded collagenous material.

Expanded collagenous materials can be used to prepare a wide variety of graft elements useful in certain inventive devices. Methods for preparing such elements can include contacting an ECM or other collagenous starting material with an alkaline substance in an amount effective to expand the material, casting or otherwise forming the expanded collagenous material into a particular shape (e.g. an elongate tube or cylinder or a plug-like segment), and lyophilizing the expanded material to form a dried graft body.

ECM tissue layers can be used in the manufacture of laminated graft body structures, For these purposes closure element 110 can for example be comprised of about 1 to 10 extracellular matrix tissue layers. Sheets of multilaminate ECM tissue layers can be prepared in any suitable fashion. These include, for instance, dehydrothermal bonding under heated, non-heated or lyophilization conditions, using adhesives, glues or other bonding agents, stitching, crosslinking with chemical agents or radiation (including UV radiation), or any combination of these with each other or other suitable methods. For additional information as to techniques for laminating ECM layers to one another, reference may be made for example to U.S. Pat. Nos. 5,711,969, 5,755,791, 5,855,619, 5,955,110, 5,968,096, and to U.S. Patent Publication No. 20050049638.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present disclosure, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

The invention claimed is:

1. A method for obstructing a perivalvular leak, the method comprising:
   delivering a closure device to a perivalvular leak, the leak defining a space between a valve and patient tissue, said closure device comprising an elongate strip of bioresorbable tissue infiltratable material sized and configured to transverse a perivalvular leak, said closure device also containing one or more filaments slidably associated with said material at a plurality of locations;
   inserting the closure device through the perivalvular leak, such that a first portion of said closure device protrudes on a distal side of the perivalvular leak, a second portion of said closure device extends through the perivalvular leak between the external surface of the valve and patient tissue, a third portion of said closure device protrudes on a proximal side of the perivalvular leak; and
   deforming said elongate strip such that said first portion gathers substantially over the distal side of the perivalvular leak, and said third portion gathers substantially over the proximal side of the perivalvular leak.

2. The method of claim 1 wherein:
   said bioresorbable tissue infiltratable sheet material comprises extracellular matrix material.

3. The method of claim 1 further comprising:
   attaching said closure device to the vessel wall.

4. The method of claim 1 further comprising:
   securing the position of said closure device on said filament.

5. The method of claim 1 further comprising:
introducing a capping element over said filament, wherein said capping element contains a filament channel which receives said filament.

6. A method for obstructing a perivalvular leak between patient tissue and an implanted heart valve, the method comprising:
inserting a cannulated device through the perivalvular leak from a proximal side to a distal side;
deploying a first portion of a closure device from the cannulated device on the distal side of the perivalvular leak, said closure device comprising a strip of bioresorbable tissue infiltratable material sized and configured to transverse a perivalvular leak, said closure device also containing one or more filaments slidably extending through a plurality of openings;
deforming said first portion to an expanded cross-sectional profile;
retracting said cannulated device through the perivalvular leak;
deploying of a second portion of said closure device extending through the perivalvular leak and protruding on the proximal side of the perivalvular leak; and
deforming said second portion to an expanded cross-sectional profile.

7. The method of claim 6 wherein:
said bioresorbable tissue infiltratable sheet material comprises extracellular matrix material.

8. The method of claim 6 further comprising:
attaching said closure device to the vessel wall on the distal side of the perivalvular leak.

9. The method of claim 6 further comprising:
attaching said closure device to the vessel wall on the proximal side of the perivalvular leak.

10. The method of claim 6 further comprising:
securing the position of the closure device on the filament such that the closure device maintains the expanded cross-sectional profile.

11. The method of claim 6 further comprising:
introducing a capping element over said filament, wherein said capping element contains a filament channel which receives said filament.

12. A method for obstructing a perivalvular leak associated with an implanted artificial valve, the method comprising:
inserting a closure device into a perivalvular leak, the perivalvular leak comprising a gap between patient tissue and an implanted artificial valve, the artificial valve having an outer surface, wherein the perivalvular leak comprises a passage between a first opening defined by the outer surface of the artificial valve and patient tissue and a second opening defined by the outer surface of the artificial valve and patient tissue, and wherein the closure device comprises a bioresorbable tissue infiltratable material sheet, and wherein said inserting causes a first portion of the closure device to extend from the first opening of the perivalvular leak and a second portion of the closure device to extend from the second opening of the perivalvular leak with an intermediate portion extending between the first and second openings transversing the perivalvular leak passage; and
deforming the closure device so as to cause the bioresorbable tissue infiltratable material sheet to push against the outer surface of the artificial valve and patient tissue so as to occlude the perivalvular leak.

13. The method of claim 12, wherein:
said deforming causes the first portion of the closure device to form a first gathered region over the first opening of the perivalvular leak.

14. The method of claim 13, wherein:
said deforming also causes the second portion of the closure device to form a second gathered region over the second opening of the perivalvular leak.

15. The method of claim 12, wherein:
said deforming is caused by tensioning a filament, the filament attached to and slidably associated with the bioresorbable tissue infiltratable material sheet.

16. The method of claim 12 wherein:
said bioresorbable tissue infiltratable sheet material comprises extracellular matrix material.

* * * * *